United States Patent [19]
Friedman

[11] Patent Number: 5,676,691
[45] Date of Patent: Oct. 14, 1997

[54] TREATMENT OF VASCULAR AND TENSION HEADACHE, ATYPICAL FACIAL PAIN, AND CERVICAL MUSCLE HYPERACTIVITY

[76] Inventor: Mark H. Friedman, 75 Barnard Rd., New Rochelle, N.Y. 10801

[21] Appl. No.: 665,008

[22] Filed: Jun. 17, 1996

Related U.S. Application Data

[63] Continuation-in-part of Ser. No. 311,009, Sep. 21, 1994, Pat. No. 5,527,351.
[51] Int. Cl.⁶ ........................................................ A61F 7/00
[52] U.S. Cl. ................................................................. 607/96
[58] Field of Search ............................ 607/96, 108–112, 607/114; 601/15, 148

[56] References Cited

U.S. PATENT DOCUMENTS

| | | | |
|---|---|---|---|
| 1,860,847 | 5/1932 | Armstrong | 607/109 |
| 2,101,628 | 12/1937 | Padelford | 607/109 |
| 4,527,565 | 7/1985 | Ellis | 607/109 |
| 4,920,963 | 5/1990 | Brader | 607/109 |
| 5,527,351 | 6/1996 | Friedman | 607/96 |

OTHER PUBLICATIONS

Self-Care, Spring 1993 Catalog – Excerpt for Face Shield.
Bernard et al, "Cryosurgery in the Management of Intractable Facial Pain," *British Journal of Oral Surgery*, vol. 16, No. 2, pp. 135–142, Nov. 1978.
Bernard, "The Effects of Extreme Cold on Sensory Nerves," *Annals of the Royal College of Surgeons of England*, vol. 62, pp. 180–187, 1980.

*Primary Examiner*—Robert Nasser
*Attorney, Agent, or Firm*—Evelyn M. Sommer

[57] ABSTRACT

A new method for treatment of vascular headaches (migraine and cluster), tension headache, atypical (chronic) facial pain, and cervical muscle spasm is presented. This method comprises the application of cold water or saline (0°–4° C.), cold metal or ice to the area of tenderness associated with the plexus formed by the posterior superior alveolar branch of the ipsilateral maxillary nerve, as well as to other branches of the trigeminal nerve. Immediately preceding the application of the cold, an injection of a conventional dental anesthetic in the conventional amount used for that purpose can be made. The cold or frozen water or saline can be applied indirectly when contained in small bags, tubes or packets made of plastic film, latex, silicone, or the like. Metal tubes can also be used which have been chilled by either passing cold water or ice through their hollow interiors. Plastic tubes encasing a column of ice, which ice can be extruded gradually by the patient or clinician by means of a plunger inserted into the tubes can also be advantageously used. The cold treatment even without the use of the dental anesthetic is effective if the treatment time with the cold is extended to from about 20 to about 40 minutes. Alleviation of pain is noted within a short period of the onset of the treatment. Repeated treatment even during pain free periods offers protracted benefits, i.e., prevention or amelioration of the headaches or other conditions.

18 Claims, 6 Drawing Sheets

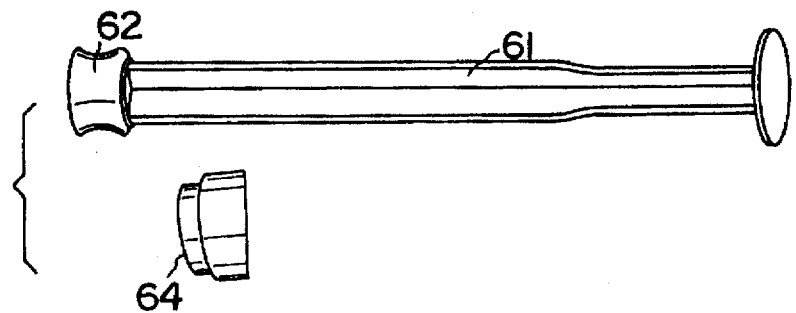
F I G. 10
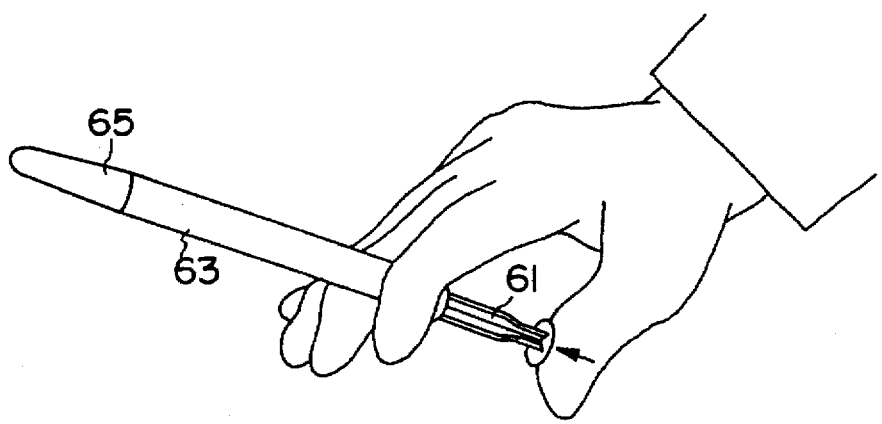
F I G. 11
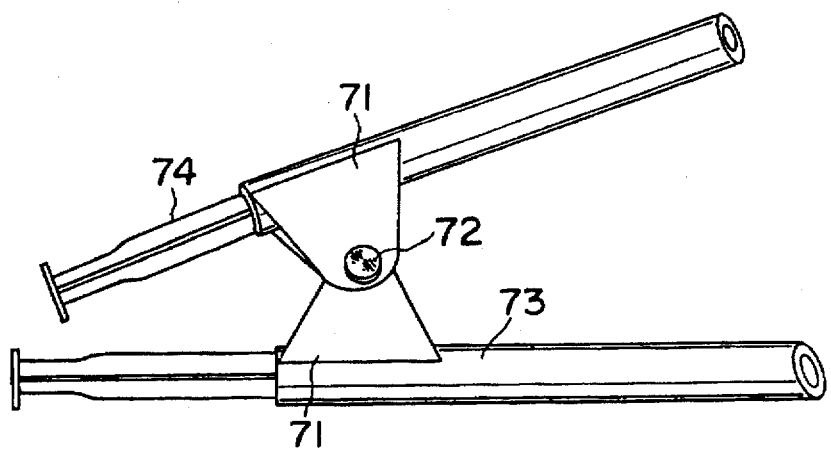
F I G. 12

TREATMENT OF VASCULAR AND TENSION HEADACHE, ATYPICAL FACIAL PAIN, AND CERVICAL MUSCLE HYPERACTIVITY

This application is a continuation-in-part of application Ser. No. 08/311,009, filed Sep. 21, 1994, now U.S. Pat. No. 5,527,351.

The present invention relates to a new method for treatment of vascular (migraine, cluster) and tension headache, chronic facial pain, and cervical muscle hyperactivity (spasm).

The method is non-toxic, and non-sedating.

The method of the invention comprises the application of cold water or saline (0°–4° C.) to an area of intraoral tenderness, which tenderness has been found to be associated with the aforesaid conditions, sometimes in conjunction with the injection of a local dental anesthetic agent. The zone of tenderness has been observed by the inventor to be in the area of the plexus formed by the posterior superior alveolar branch of the ipsilateral maxillary nerve, and is bilateral when the symptoms are bilateral.

The cold water is applied indirectly to the maxillary nerve (V2), a division of the trigeminal nerve, by perfusing the cold water through hollow metal tubes, or by direct application of ice extruded from hollow plastic or metal tubes. In the latter instance, a device is preferably provided wherein the ice can be extruded gradually by the patient or physician into contact with the area overlying the nerve. Frozen saline can also be applied contained within small plastic bags.

The applicant's earlier patent application described the application of cold alone to the zone of intraoral maxillary tenderness and the finding that such treatment produced a decrease in the frequency and severity of headaches, facial pain and cervical spasm, in symptomatic patients and that longer lasting relief could be obtained by repeating the procedure. In the earlier application, the cold was applied for up to seventeen minutes.

The applicant has now found that if a local anesthetic of the type conventionally used by dentists for injection into oral tissue to produce pain free dental treatment is injected into this same zone of intraoral maxillary tenderness immediately preceding the initiation of the treatment with cold, the onset of decrease in symptomatology and duration of benefits is improved in chronic daily (constant) headache, post-traumatic headache, and acute migraine and tension-type headache.

In addition, the applicant has found that additional benefits are realized by increasing the time of the cold application to approximately 20–40 minutes, even if the use of the local anesthetic is omitted.

The addition of local anesthetic to the maxillary tender zone just before the treatment with cold has two main advantages over treatment with cold only: (1) it is more effective in relieving acute headache symptoms, (2) repetitive treatment with this technique is also effective in reduction/elimination of headaches such as chronic daily headache, post-traumatic headache conditions, that have proven unresponsive to conventional treatment or application of up to seventeen minutes of cold alone.

Chronic daily headache (CDH) is defined as a constant tension type headache usually with migrainous exacerbations. CDH usually evolves over time from episodic migraine, but its cause is still unknown. CDH is refractory to conventional treatment. Individuals suffering from CDH frequently suffer from rebound headache as well, i.e., the worsening of headache pain in chronic headache sufferers, caused by the frequent and excessive use of ergots and non-narcotic analgesics.

In post-traumatic headache, in addition to the immediate pain following a head injury, a more prolonged and enduring headache may develop. This condition, resembling either migraine or tension headache, may last for weeks, months or years.

The presence of the epinephrine, the most commonly used vasoconstrictor in the local anesthetic is not solely responsible for the advantages resulting from this combined technique. In patients who cannot take epinephrine for medical reasons, instillation of a local anesthetic without epinephrine (such as Carbocaine) is still beneficial. Breaking the pain cycle enables the cold to be more effective. Additionally, the local anesthetic is also a NA+ blocking agent that reduces or eliminates conduction in the thinner pain fibers.

Cervical muscle hyperactivity (spasm) has been found to be responsible for the circumscribed sterile inflammation, giving rise to the intra-oral tenderness, which sends nociceptive impulses to the cervical area, perpetuating pain and muscle spasm. This "vicious cycle" is similar to that occurring when a muscle in sustained contraction creates nociceptive substances (lactic acid, substance P, etc.), causing impulses to ascend via spinothalamic tracts to the thalamus and somatosensory cortex.

The anesthetics selected for use in the invention are commonly used in dentistry and include without limitation, Xylocaine, Carbocaine, Xylocaine with epinephrine, Carbocaine with Neo-cobefrin, or Citanest.

The most common anesthetics injected by dentists today are either Xylocaine (lidocaine) or Carbocaine (mepivacaine).

Xylocaine comes in a 2 percent solution with either 1:100,000 or 1:50,000 parts of epinephrine. Epinephrine is a vasoconstrictor. A vasoconstrictor is an important component of most anesthetics. It serves two functions. First, it reduces the blood circulation in the area. This helps in surgery because there is less bleeding in the area to be surgically treated. Its other function is to keep the area anesthetized longer, since circulating blood does not remove the anesthetic from the site. This reduces the likelihood of any toxic reaction because the anesthetic is removed very slowly from the needed area. Thus, less anesthetic is needed to keep the area anesthetized. The safety record with Xylocaine is excellent. Xylocaine starts working in from instantly to four minutes after injection. The anesthetic effect lasts about two and a half hours in most patients.

Carbocaine is the second most commonly used anesthetic. Carbocaine comes in a 3 percent concentration without any epinephrine. Because of the lack of epinephrine, many cardiologists suggest this particular anesthetic be used in patients who have heart problems or are diabetic. Carbocaine's action is that it will remain in the operative site for up to about forty minutes without the hazards of adding epinephrine to the solution. It works as fast and as effectively as Xylocaine.

Xylocaine, Carbocaine and Xylocaine with epinephrine are preferred for use herein. If epinephrine cannot be used, based on the patient's history, a local anesthetic without epinephrine is still advantageous.

As previously described, Carbocaine (or mepivacaine) may be administered in a 3 percent solution without epinephrine. The latter is now also available in a 2 percent solution with a vasoconstrictor called Neo-cobefrin. Vasoconstrictors keep the anesthetic solution in the area for a longer duration because they limit the blood flow in the area of the injection. An added advantage of vasoconstrictors is that they restrict bleeding during surgical procedures.

Neo-cobefrin increases the duration of anesthesia up to one to two and a half hours in the upper jaw and two and a half hours in the lower jaw. Contrast these figures to twenty minutes in the upper jaw and forty minutes in the lower jaw when the Neo-cobefrin is omitted. The onset of anesthesia ranges, in both instances, is from thirty seconds to four minutes.

Carbocaine containing Neo-cobefrin has many of the same concerns as anesthetics containing epinephrine. Caution should be used in injecting patients with Carbocaine containing Neo-cobefrin if the patient has a history of high blood pressure, heart disease, or diabetes.

Citanest (prilocane) in a 4 percent solution is used in many offices for patients who cannot tolerate the epinephrine in most anesthetics. Citanest with 1:200,000 epinephrine can also be used for patients requiring minimal epinephrine. The onset of action takes one to two minutes, and the anesthesia lasts about an hour or slightly longer in some cases.

It is not recommended that Citanest be used in infected areas or in children under the age of ten. In addition, patients with liver damage or patients who are severely ill should not be treated with this anesthetic as Citanest is metabolized by the liver, liver damage can be a contraindication to its use.

All of the anesthetics discussed above are safe and reliable when used with proper precautions.

The combined (cold plus anesthetic) treatment produces a marked decrease or elimination of the intra-oral maxillary tenderness and, with repeated applications, a decrease in frequency and severity of headaches. When the patient is symptomatic, headache, facial pain, and cervical spasm relief, occurs. If the pain returns, or to provide more long lasting relief, the procedure is repeated. The findings confirm enhanced results over the use of cold alone with the relief being of more rapid onset and of longer duration, and frequently more profound.

Headaches can be classified into three main groups: muscle contraction (tension-type), vascular (migraine, cluster), and inflammatory headaches. The latter group may be caused by stroke, hypertension, hemorrhage from an aneurysm, brain tumor, infections, or inflammation.

Tension-type headache (new International Headache Society classification), formerly referred to as muscle contraction headache, is by far the most common headache. This condition is divided into two major categories, episodic tension-type headache and chronic tension-type headache. The former is the familiar ailment that virtually everybody experiences occasionally. The latter condition may be related to migraine. It is characterized by daily or almost daily discomfort with superimposed migrainous events at varying frequencies, and may be the most common problem seen at headache centers. Patients complain of daily headache, which is dull to moderate most of the time, except for several days during the month when they are partly or completely incapacitated. At such time, pain is associated with typical migrainous symptoms such as nausea and vomiting, photophobia, and other descriptors of migraine. Patients usually complain of pain and tightness in the frontal, temporal and/or occipital areas. The latter area may indicate cervical involvement. The definition of "tension-type" headache is confusing, because it does not distinguish between psychological tension and muscle tension induced headache. It is noted that muscle tension cannot be consistently demonstrated in tension headache patients. Some authorities believe that psychological factors, including stress, cause muscle tension which produces the headache. Additionally, many of these same patients exhibit significant cervical muscle spasm and/or inflamed cervical joints often associated with arthritis, which can refer directly as tension-type headache. Other factors such as postural deformities or poor work habits can also contribute to the headache directly or by causing adjacent craniofacial muscle spasm or temporomandibular joint inflammation, thereby contributing indirectly to the tension-type headache.

Treatment for headache includes physical therapy, biofeedback, chiropractic, counseling, and medication. The latter includes analgesics, muscle relaxants, tranquilizers, and antidepressants. Combination drugs are widely used. Many of these patients tend to abuse a wide variety of medications, including both prescription and non-prescription drugs. Overuse often leads to an analgesic rebound headache or the worsening of head pain caused by the frequent and excessive use of analgesics.

Migraine is the most common headache causing patients to consult physicians. Based largely on data drawn from the American Migraine Study, in which over 20,000 respondents returned questionnaires mailed to their households, the results indicate migraine occurs in 17.6% of females and 6% of males in the United States. Considering this incidence, the economics of migraine in time lost from work, inefficiency, etc. is substantial. Effective treatment increases the patient's ability to live a normal and productive life. In addition to pain, the symptoms most commonly associated with migraine include nausea and vomiting, photophobia, phonophobia, anorexia, pallor, and a desire to lie down. If symptoms are preceded by or associated with visual symptoms such as flashing lights, black spots or partial visual field loss, the migraine is classified as classic, as opposed to the previously described common migraine. New terminology for identifying these headaches are migraine with aura and migraine without aura, respectively.

Multiple humoral agents have been postulated as being the major factor in migraine. These include serotonin, histamine, prostaglandins, platelet factors, endorphins, and vasoactive neuropeptides. The etiology of migraine has been studied by many investigators. Present research no longer supports the vasodilator/vasoconstrictor mechanism of vascular headache, i.e., arterial dilation causes pain and constriction equals relief. Research has now implicated a sterile inflammation, possibly occurring in the meninges (pia mater, dura mater, arachnoid), as the causative factor for vascular head pain. An unknown trigger activates perivascular trigeminal axons, which release vasoactive neuropeptides (substance P, calcitonin gene-related peptide, etc.). These agents produce the local inflammation i.e., vasodilatation, increased capillary permeability, plasma extravasation, causing transmission of impulses to the brain stem and higher centers, which in turn register as head pain (Moskowitz M. A., Trends in Pharmacological Sciences, August 1992).

Migraine therapy is either prophylactic or symptomatic. Prophylactic medication may be selected for a patient having 2–4 or more headaches per month, if they are severe enough to interfere with daily activities. Beta blockers such as propranolol (Inderal) are the most common. Other medications often used are serotonin antagonists such as methysergide maleate (Sansert), calcium channel blockers (Verapamil), amitriptyline (Elavil), and ergotamine preparations with belladonna alkaloids and phenobarbital. These all have significant side effects including sedation, loss of energy and drive, dry mouth, constipation, weight gain, and gastrointestinal cramping and distress. For symptomatic treatment, ergotamine with caffeine (Cafergot) is commonly used. Other medications employed for treating migraine include isometheptene mucate (Midrin), NSAID's (Motrin, Naprosyn, etc.), dihydroergotamine and the newer medication sumatriptan (Imitrex), the last two having to be injected intramuscularly. When narcotics, such as Fiorinal with codeine are used frequently, additional hazards including the considerable potential for rebound headaches and habituation are encountered.

Cluster headaches occur much less frequently than migraine, and mostly (90%) in men, who usually complain of severe unilateral eye pain, ptosis (drooping eyelid), eye tearing, and nasal congestion and/or discharge. Unlike migraine patients, who feel more comfortable when lying down, these patient's symptoms usually increase in a supine position. These relatively brief but severe headaches occur daily (or even more frequently) during the cluster period, which may last for several months.

The mechanism for cluster headache may be a pathophysiologic event occurring within the intracavernous carotid artery that activates nerve fibers within the pericarotid plexus. This plexus receives axonal projections from V1 and V2, superior cervical ganglia (sympathetic), and sphenopalatine (parasympathetic) ganglia. Trigeminal projections are activated to transmit impulses centrally and mediate periorbital, retro-orbital, and forehead pain.

Cluster headache therapy includes: steroids (Prednisone), Sansert, Verapamil, various ergot compounds, and lithium (for chronic cluster headaches). All of these medications can produce serious side-effects and complications. Inhalation of oxygen at the headache onset has been found in some cases to abort the headache, but this technique is not available if the headache occurs when the subject is away from home.

Other modes for treating these various types of headaches include: (a) acupuncture, (b) biofeedback, and (c) chiropractic. Studies have failed to show that acupuncture and chiropractic are more effective than placebo. Acupuncture requires a highly-trained therapist. Biofeedback (training in muscular relaxation) may be helpful for tension-type headache in selected individuals, but controlled studies have not demonstrated consistent success in the above conditions.

Atypical facial pain, which has recently been classified as facial pain by the International Headache Society, manifests itself as a relatively constant, mostly unilateral (at least initially) pain unrelated to jaw function. This condition is not associated with sensory loss or other physical signs, and radiographic and laboratory studies are uniformly negative. This condition may occur as a residual from relatively uncomplicated dental work, but usually the cause is unknown. Many neurologists regard this condition as psychogenic. Amitriptyline at bed-time and/or various analgesics and narcotics are used, but atypical facial pain responds poorly to all forms of medication.

Cervical muscle hyperactivity (spasm), is an extremely common condition with many causes, including tension, response to an inflamed or subluxed joint, arthritic changes, poor posture or work habits, trauma, systemic disease and adjacent pathology. Common treatment modalities are physical therapy, chiropractic, and medications, including muscle relaxants, NSAID's, analgesics, and anti-depressants in small doses. Often, despite all efforts made to alleviate this type of spasm, the condition becomes chronic. When a cervical joint becomes subluxed, it causes pain and restricted motion, local inflammation, and adjacent muscle spasm. Manipulation to unlock the joint is indicated, but muscle spasm should be reduced first. Conventional methods of treatment include heat, ultrasound, electrogalvanic stimulation, and massage. All of these methods are obviously time consuming. The relation between the condition of cervical muscle spasm and the previously described headaches and facial pain can be demonstrated by the fact that the headache and facial pain patients do not respond as well to treatment in the presence of significant cervical muscle spasm. One reason may be entrapment of the greater occipital nerve by semispinalis muscle spasm. This greater occipital nerve supplies the cranial vertex.

The need for a more appropriate method of treating vascular and tension headaches, atypical facial pain, and cervical muscle spasm is apparent as the current methods of treatment are often ineffective. Treatment with pharmacological agents is associated with toxicity and must be used systemically over prolonged periods of time and often for decades. These agents further do not meet with patient acceptance or compliance. The conditions herein described represent a tremendous economic loss, considering the number of individuals afflicted, the time lost from work, as well as the inability to enjoy a normal pain-free life.

Even though present research has strongly implicated a sterile perivascular inflammation as responsible for vascular headaches, the postulated site for this occurrence, the meninges, has not been confirmed.

The inventor's research strongly suggests that this phenomenon occurs elsewhere and specifically in the previously described ipsilateral maxillary nerve plexus, and that it is also implicated in tension headaches, atypical facial pain, and cervical muscle spasm. It is likely that edema occurs in the maxillary nerve plexus microcirculation, caused by vasodilatation and increased vascular permeability. This edema causes pressure on nerve endings which creates local tenderness and pain. Because of this area's relative accessibility, it has been possible to consistently demonstrate several elements of local sterile inflammation:

(1) normal appearing tissue,
(2) consistent tenderness, which is strongly related to laterality and severity of symptoms,
(3) increased temperature, and
(4) positive response to cold.

No obvious tissue pathology or periodontal condition was noted in examination of over 800 patients with the above conditions. Even periodontal lesions of the maxillary molars, present in a few of these 800 patients (n=6) were located much closer to the gingival line, and appeared unrelated to the maxillary tender zone in the area of the root apices.

In one procedure, blinded, inexperienced observers, correctly identified the symptomatic side in 178/200 (89%) of symptom-free migraine and cluster headache patients by intraoral palpation to determine the laterality of the maxillary tenderness. In over 90% of headache and facial pain patients observed by experienced investigators, ipsilateral tenderness, even in the symptom-free state, was found in patients presenting histories of such symptoms. It was found that bilateral symptoms produced bilateral tenderness, directly proportional to symptom severity. Tension headache usually occurs bilaterally, and these cases invariably demonstrated bilateral tenderness. The tender zone in patients with cervical muscle spasm was similarly related to laterality and severity of symptoms. In 36/38 tension headache patients experiencing unilateral symptoms, a 94.7% correlation was found between laterality of symptoms and tenderness. The tender zone in patients with cervical muscle spasm was similarly symptom related.

Temperature increase was also associated with intraoral maxillary tenderness. In fifty consecutive symptomatic patients with complete or significant unilaterality of symptoms, ipsilateral intraoral maxillary zone tenderness and temperature was demonstrably higher than on the ipsilateral side in 46/50 cases. A model YSI (Yellow Spring Instrument Co.) 43TA tele-thermometer with #406 probe was used. Significantly, the temperature differential between left and right sides appeared directly proportional to degree of tenderness and severity of symptoms. In extreme cases, the temperature differential between left and right sides was as much as 2.1 degrees Fahrenheit. In 15 consecutive normal patients, occasional minimal tenderness and temperatures which were nearly or completely identical bilaterally were observed.

In accordance with the invention, there is disclosed a method for treating vascular and tension headaches, atypical facial pain, and cervical muscle hyperactivity comprising applying cold to the area of maxillary alveolar tenderness, a common finding associated with the plexus formed by the posterior superior alveolar branch of the maxillary nerve, as well as to other branches of the trigeminal nerve in subjects having such conditions preceded by or simultaneously with the application of cold, an injection directly into this same area of a member selected from the group of Xylocaine, Carbocaine, Xylocaine with epinephrine, Carbocaine with Neo-cobefrin, or similar anesthetic in a dental pain relieving amount. The application of cold, together with the injection of a dental anesthetic was utilized in over 250 office procedures in strongly symptomatic patients. Significant or total relief was obtained in over 80% of the patients. Daily treatment of a group of twenty patients, whether or not the patient was symptomatic, resulted in improvement, i.e., decrease in the frequency, intensity or duration of headaches or facial pain in over 65% of patients.

It is theorized that lowered tissue temperature and the use of the anesthetic, particularly when epinephrine or an equivalent is present reduces vasodilatation, thereby resolving the plasma extravasation (edema) which reduces pressure on the maxillary nerve as well as interrupting the pain cycle. In the majority of patients with cervical symptoms and tenderness, a significant reduction of cervical symptoms, increased cervical range of motion, and decreased posterior cervical electromyographic (EMG) signal reduction during the combined cold/anesthetic application was noted. It was additionally found that by increasing the cold application time to approximately 40 minutes, additional benefits were observed, even without addition of local anesthetic.

Such benefits include:
1. Significantly better results in eliminating acute migraine and tension-type headaches, even if symptoms had lasted for several days. In the recalcitrant headaches, greater improvement was noted during minutes 20–40 of application, than in the first 0–20 minutes. Additionally, these acute headaches were less likely to return when the additional treatment time was utilized, even without addition of a local anesthetic.
2. Some non-responsive cervical muscle spasm cases also responded positively with increased treatment time.

This invention will be further explained in reference to the figures wherein:

FIG. 10 illustrates two parts of an extrusion device which are a plunger and stopper, the plunger at its proximal end being provided with an attachment for facilitating extrusion, and a rubber stop. The device is used in conjunction with a cylinder (hollow plastic tube).

FIG. 11 shows a further embodiment of the device of FIG. 10 and consisting of a hollow plastic tube assembled for use with the stopper removed, the plunger inserted and the ice emerging from the device; and FIG. 12 shows two of the devices of FIG. 11 joined by a pivotable connecting means.

Figure 1:
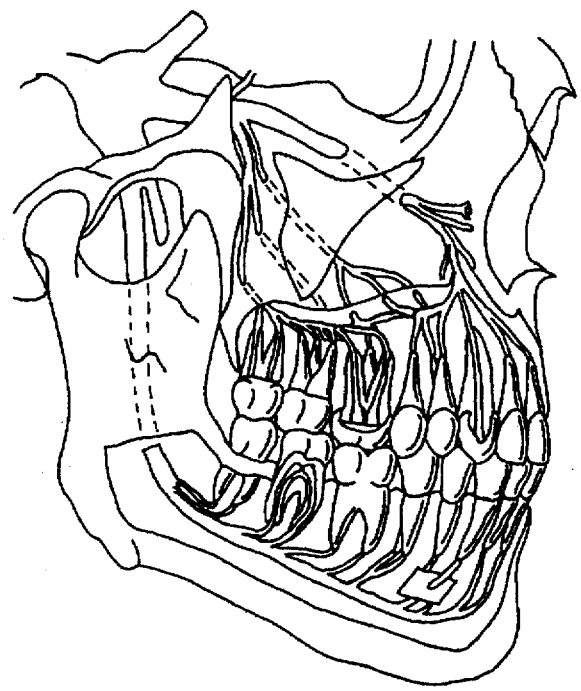
FIG. 1 illustrates the distribution of the trigeminal nerve.

The treatment of acute headache poses problems for physicians in that:
1. If a narcotic is given for relief, patients usually require additional anti-nausea medication.
2. If relief is not adequate, more narcotic may be prescribed, requiring observation for several hours to assess relief.
3. Patient dismissal is problematic. Since narcotics are CNS depressants, it may not be safe to allow the patient to drive.
4. If the patient is medically compromised or pregnant, narcotics or headache medications may create further problems.
5. Imitrex, a relatively easy acute medication to administer, has a headache reoccurrence rate (average 9.1 hours) of 46.5%. Additionally, it is not very effective on longer-lasting headaches and should not be used with many medical conditions.

The instant invention provides a method for solving the physician's problem and namely, the application of cold to the area of intraoral tenderness associated with this condition in conjunction with a local dental anesthetic. The application of cold in this case amounting to up to 17 minutes. By increasing the application time of the cold to about 20 to about 40 minutes, the same results are realized with no local anesthetic being administered.

Clinical evaluation of a non-toxic, non-sedating method for treatment of migraine and tension headache, atypical (chronic) facial pain, and cervical muscle spasm comprising the application of cold water or saline (0°–4° C.), cold metal or ice to the area of tenderness associated with the plexus formed by the posterior superior alveolar branch of the maxillary nerve, as well as to other branches of the trigeminal nerve, sometimes immediately preceded by an injection of a dental anesthetic selected from the group of, Xylocaine, Carbocaine, Xylocaine with epinephrine, Carbocaine with Neo-cobefrin, or Citanest in the conventional amount used by the dentist to produce anesthesia, was carried out In over 250 in-office applications to symptomatic patients with the above conditions, significant or total relief was obtained in over 80% of the patients. Each of the cold applications ranged from 30 to 60 seconds when the small plastic packets were used, for about 2 to about 6 minutes when the plastic or metal extrusion tubes were used, and up to about 30 to 40 minutes (usually bilaterally) with the flowing cold water. The injection of dental anesthetic sometimes immediately preceded cold application. Daily applications, whether or not the patient was symptomatic, appeared to have protracted benefits. Frequency, intensity, or duration of headaches or facial pain improved in over 80% of patients. Significant improvement occurred when the plastic ice-filled extrusion tubes were used, or the metal tubes with the flowing cold water were used bilaterally, by patients (N=9) at home for 15 to 20 minutes.

Results of the clinical evaluations provided information in support of the proposed neurologic and physiologic mechanism of the pain associated with migraine and tension headaches, atypical facial pain and cervical muscle spasm. Because of the relative accessibility of the maxillary nerve plexus, as previously noted, it was possible to consistently demonstrate several elements of local sterile inflammation, i.e., (1) normal appearing tissue, (2) consistent tenderness in that area that was strongly related to symptoms, (3) increased temperature associated with area of tenderness, and (4) positive response to treatment with cold.

Figure 2:
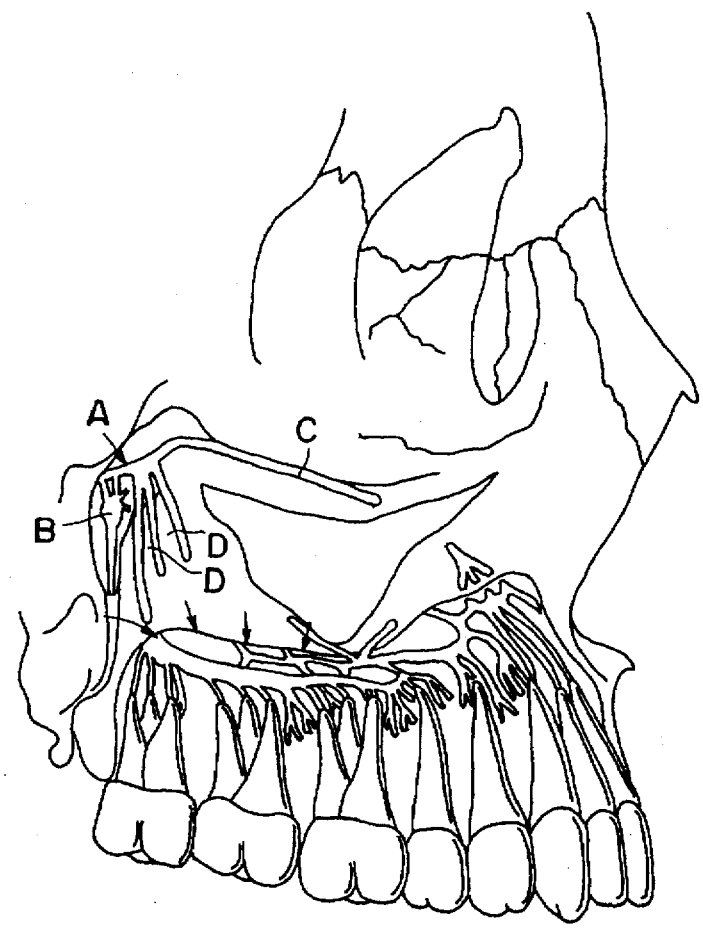
FIG. 2 illustrates the maxillary division (V2) of the trigeminal nerve.
Figure 3:
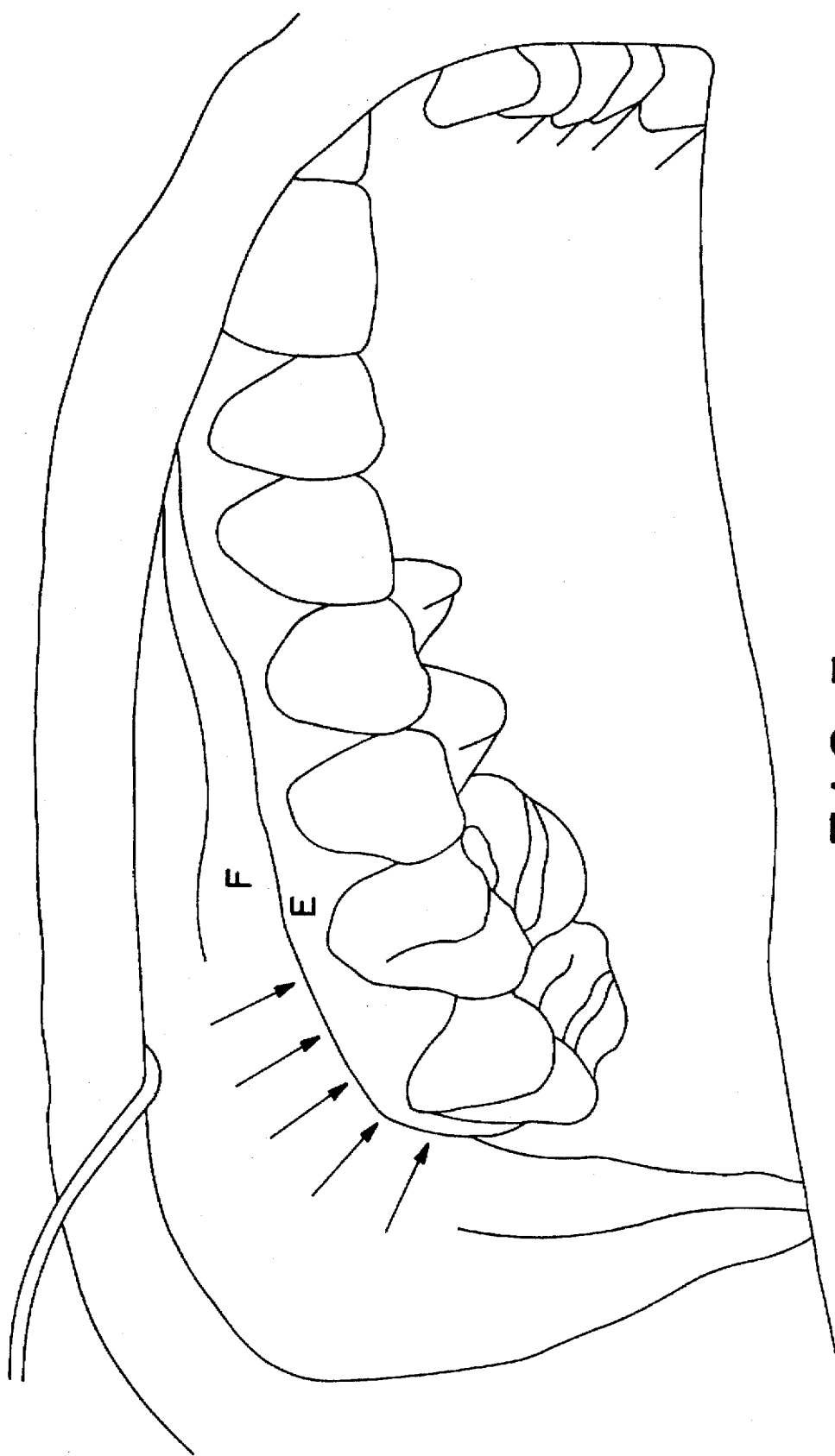
FIG. 3 illustrates the location of the intra-oral zone of maxillary tenderness.

FIGS. 1-3 are anatomical drawings. FIGS. 1-2 show the distribution of the trigeminal nerve and the maxillary division (V2) of the trigeminal nerve, respectively. In FIG. 2, the plexus formed by the posterior superior alveolar branch of the maxillary nerve is shown. In this figure the reference symbol A represents the maxillary nerve, B, the sphenopalatine ganglion, C, the infraorbital nerve and D the posterior and middle superior alveolar branch of the maxillary nerve. The arrows mark the plexus formed by the maxillary nerve branches.

FIG. 3 illustrates the location of the intra-oral zone of maxillary tenderness of one side of the face. The arrows represent the zone of tenderness. E designates the attached gingiva and F, the alveolar mucosa.

Figure 4:
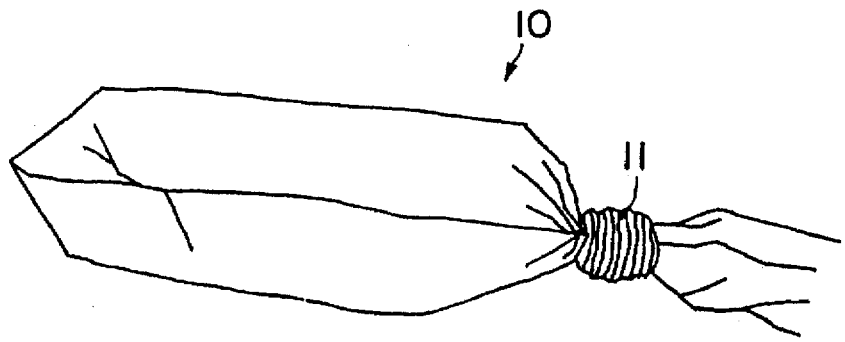
FIG. 4 illustrates a plastic film packet (¼"×1") filled with saline solution.

Referring to the drawing, FIG. 4 shows a small plastic bag 10 approximately about 1" in length and ¼" in diameter which has been prefilled with water or saline and has been sealed as by a knot 11 or by heat sealing to avoid leakage of the liquid contents. The individual bags may be refrigerated until needed. The bags may also be prepared in a continuous chain (not shown), the connecting areas between bags having been sealed by heat and/or pressure. Individual bags can be separated off as then needed. The plastic used for forming the bags can be any of the conventional plastics, impermeable to liquid and suitable for insertion into the mouth.

Figure 5:
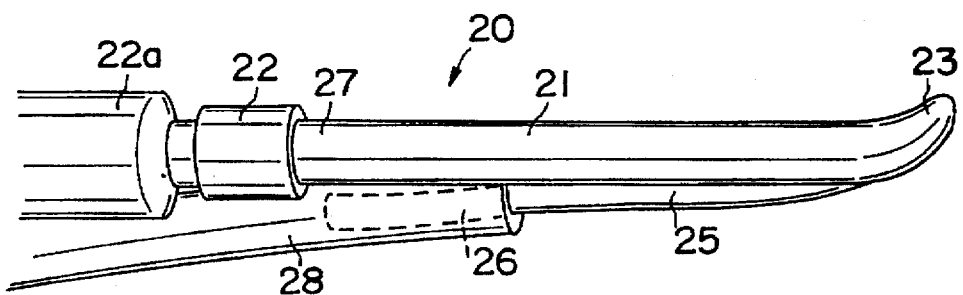
FIG. 5 illustrates a metal device consisting of two joined hollow tubes adapted for cycling of water through the two tubes.

In FIG. 5, a metal device 20 for delivering i.e., transmitting cold to the zone of intra-oral tenderness is shown. The device can be made of any non-rusting easily fabricable metal. The device is formed of a hollow metal tube 21 closed at its exposed end 23 connected to tube 25 closely adjacent to its end 23. The hollow metal tube 21 is connected to tube 25 by conventional fabrication means. Tube 21 is connected at 27 by conventional means 22 at its proximal end so that leakage of fluid does not occur when the cold water after having been perfused through the tube 25 and from there into tube 21 is returned for chilling. The cold water enters during the application of the device into direct contact with the zone of intraoral tenderness via the structure shown at 25, from there into tube 21, the end of which 23 is in contact with the intraoral zone of tenderness, moving from that portion of the structure into the flexible tubing (not shown) for recycling to a chill zone and back to tube 25. 22a serves to facilitate gripping of the device in use.

The structure as described facilitates the continuous recycling of the water throughout the procedure. It most conveniently provides a means for removing the cold water without any attendant discomfort or inconvenience to the patient.

Figure 6:
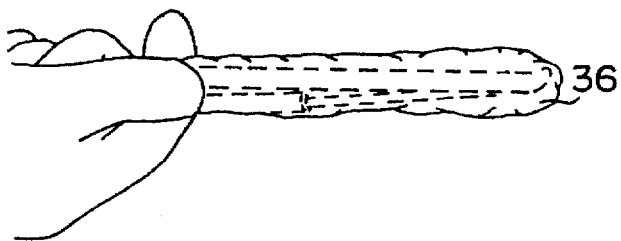
FIG. 6 illustrates a disposable plastic film sheath for use with the device of FIG. 5.

In FIG. 6, a disposable sheath 36 made of plastic film is shown which is dimensioned so that it will fit over the metal tubes 21 and 25, shown in FIG. 5. The plastic sheath 36 can be easily placed over the metal tube and removed therefrom. A new sheath can be applied and removed for each separate subject In FIG. 7 two of the devices here indicated by reference numeral 42 as also shown in FIG. 5 are provided so that the application of cold can be carried out bilaterally. The devices are provided with appropriate tubing 43 and 44 for supplying cold water and for conducting the same away once used. The arrangement is best maintained within a flask or container and pumping means are provided for maintaining the circulation of the fluid. The pump is covered by ice 45 and water.

Figure 8:
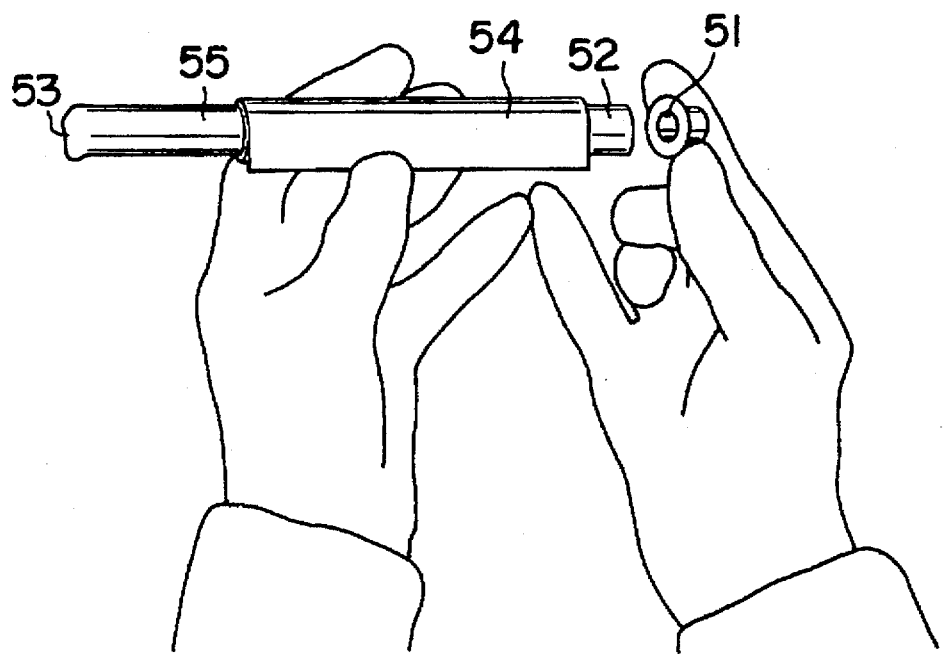
FIG. 8 illustrates a metal tube with the end shaped to adapt to the area of intraoral maxillary tenderness partially enclosed within a concentrically arranged insulating tube showing the stopper adapted for insertion into the distal end of the metal tube.

FIG. 8 illustrates an embodiment of another device and as shown comprises a hollow metal tube 55 contained within an insulating sheath 54. The proximal end 53 of tube 55 which is to be applied to the zone of intra-oral tenderness is shaped for better adaptation to the area of intramaxillary tenderness. At its opposite or distal end 52, a stopper 51 for insertion into the end 52 of the device is provided which serves to retain the cold water or ice without leakage during chilling and prior to its application. Prior to use, the tube 55 is filled with water, the stopper inserted and the tube refrigerated. When the device is to be used with a patient, the end 53 is covered by a disposable plastic sheath and held against the area of intra-oral tenderness.

Figure 7:
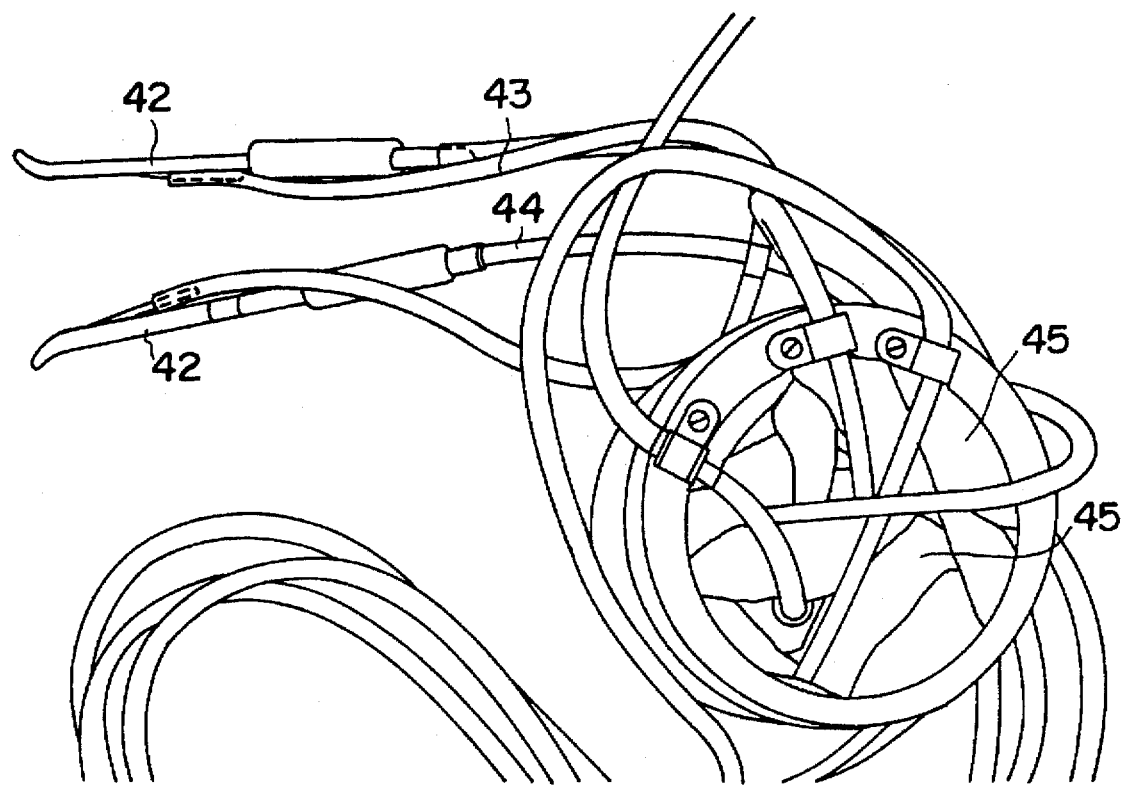
FIG. 7 illustrates two of the above devices of FIG. 5 connected in such a manner as to be able to be placed bilaterally and show a container of ice water, the devices being provided with suitable motorized pump means.
Figure 9:
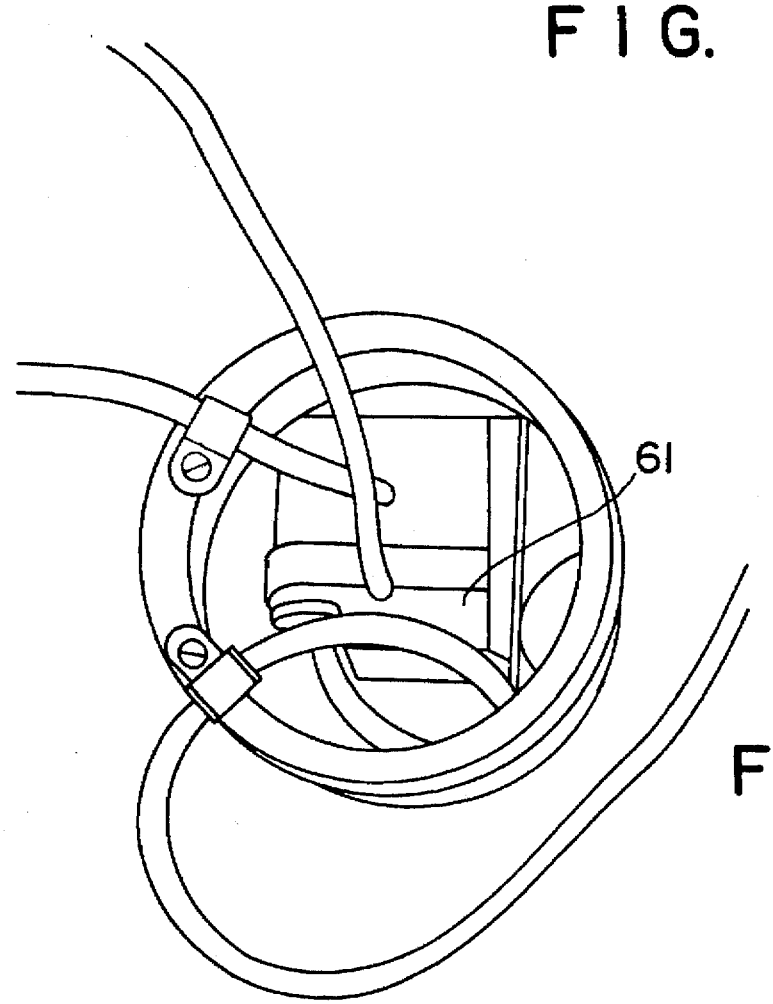
FIG. 9 illustrates another view of the device of FIG. 7 with the motorized pumping means exposed.

The pump means 61 for circulation of the cold water is shown in FIG. 9. Otherwise the device is as shown in FIG. 7.

In FIG. 10, the stopper to be used with a hollow plastic device is shown at 64. Plunger 61 is also shown in this figure and dimensioned for being received in the hollow plastic tube 63 not shown in this drawing but shown in FIG. 11. The plunger 61 is provided with a plastic or rubber tip 62 which facilitates contact between the plunger and the ice in the hollow plastic device and permits the application of more uniform pressure of the plunger onto the ice. The hollow plastic tube will be filled with water and refrigerated while maintained in an upright position for freezing the same. In use, the stopper 64 is removed, plunger 61 can then be inserted and as shown in FIG. 11, the ice 65 is extruded by hand pressure on the plunger 61. The stopper 64 is applied to the hollow tube before filling with water to prevent the escape of any fluid during chilling and can also serve as a support i.e., as a stand for the device making it convenient to use particularly for making available back up applications.

According to FIG. 12, two devices as shown in FIG. 11, are provided contained with a butterfly mounting 71 joined by an adjustable screw or pivot member 72. The mounting is adjusted through pivot 72 so that the devices can deliver cold bilaterally to the intra-oral zone of tenderness and the ice expressed by application of pressure onto the plunger 74 into and in contact with the underlying tissue. The pivot screw 72 can be set to conform to the individual anatomy of the subject being treated.

I claim:

1. In a method for medical treatment of a condition selected from the group consisting of vascular headache, tension headache, atypical facial pain, and cervical muscle hyperactivity comprising indirectly applying to a subject having such condition a cold supplying medium to the zone of intra-oral tenderness located in the area of the plexus formed by the posterior superior alveolar branch of the ipsilateral maxillary nerve of a subject having one of said conditions, the improvement being injecting a local dental anesthetic in a dental pain relieving amount into said zone of intra-oral tenderness in conjunction with the application of said cold supplying medium.

2. The improvement of claim 1, further comprising selecting said local dental anesthetic from a group consisting of Xylocaine, Carbocaine, Marcaine, Xylocaine with epinephrine, Carbocaine with Neo-cobefrin, Marcaine with epinephrine and Citanest.

3. The improvement of claim 2 wherein said local dental anesthetic is Xylocaine.

4. The improvement of claim 3 wherein said Xylocaine is in the form of a 2% solution also containing 1:50,000 to 1:100,000 parts of epinephrine.

5. The improvement of claim 2 wherein said local dental anesthetic is Carbocaine.

6. The improvement of claim 5 wherein said Carbocaine is in the form of a 3% solution.

7. The improvement of claim 2 wherein said local anesthetic is Carbocaine with Neocobefrin.

8. The improvement of claim 2 wherein said local anesthetic is Citanest.

9. The improvement of claim 1 which comprises administering said local anesthetic immediately preceding the application of said cold supplying medium.

10. The improvement of claim 1 which comprises administering said local anesthetic simultaneously with the application of said cold supplying medium.

11. The improvement of claim 1 which comprises perfusing said cold supplying medium through a hollow metal or plastic tube.

12. The improvement of claim 11 wherein said hollow metal or plastic tube is provided with a removable plastic sheathing.

13. The improvement of claim 11, further comprising a pumping means for circulating said cold supplying medium.

14. The improvement of claim 1, further comprising supplying ice as said cold medium, said ice being contained in a small tube and which method also comprises extruding said ice through said tube in direct contact with said zone of intra-oral tenderness.

15. The improvement of claim 1 wherein said condition is a vascular headache.

16. The improvement of claim 1 wherein said condition is a tension headache.

17. The improvement of claim 1 wherein said condition is atypical facial pain.

18. The improvement of claim 1 wherein said condition is cervical muscle hyperactivity.

* * * * *